(12) United States Patent
Curiel et al.

(10) Patent No.: US 6,284,742 B1
(45) Date of Patent: Sep. 4, 2001

(54) IMMUNOMODULATION BY GENETIC MODIFICATION OF DENDRITIC CELLS AND B CELLS

(75) Inventors: David T. Curiel; Bryan Walter Tillman, both of Birmingham, AL (US)

(73) Assignee: UAB Research Foundation, Birmingham, AL (US)

(*) Notice: Subject to any disclaimer, the term of this patent is extended or adjusted under 35 U.S.C. 154(b) by 0 days.

(21) Appl. No.: 09/407,511

(22) Filed: Sep. 28, 1999

Related U.S. Application Data
(60) Provisional application No. 60/102,257, filed on Sep. 29, 1998.

(51) Int. Cl.[7] ............... A61K 48/00; A61K 39/395; C07H 21/04; C12N 15/63; C07K 16/00

(52) U.S. Cl. ............ 514/44; 530/387.3; 530/388.15; 435/320.1; 435/328; 435/69.1; 536/23.5; 424/93.6

(58) Field of Search .................. 530/387.3, 388.15; 435/320.1, 328, 69.1; 514/44; 424/93.6; 536/23.5

(56) References Cited

U.S. PATENT DOCUMENTS

| 5,543,328 | 8/1996 | McClelland ............... 435/320.1 |
| 5,674,492 | * 10/1997 | Armitage et al. ............ 424/144.1 |
| 5,756,086 | * 5/1998 | McClelland et al. ............ 424/93.2 |
| 5,872,154 | * 2/1999 | Wilson et al. ............... 514/885 |
| 6,057,155 | * 5/2000 | Wickham et al. ............. 435/325 |

OTHER PUBLICATIONS

Nguyen et al., "Gene delivery into malignant cells in vivo by a conjugated adenovirus/DNA complex." Cancer Gene Therapy, vol. 4 (3): 183–190, 1997.*
Orkin et al., "Report and Recommendations of the Panel to assess the NIH Investment in Research on Gene Therapy." pp. 1–20, Dec. 1995.*
Eck et al., "Gene–Based Therapy. Goodman & Gilman's The Pharmacological Basis of Therapeutics." Ninth Edition: 77–101, 1996.*
Ledbetter et al., "Agonistic Activity of a CD40–Specific Single–Chain Fv Constructed from the Variable Regions of mAb G28.5." Critical Reviews in Immunology, vol. 17: 427–435, 1997.*
Miller et al., "Targeted vectors for gene therapy." FASEB, vol. 9: 190–199, Feb. 1995.*
Ledley F D., "Pharmaceutical Approach to Somatic Gene Therap." Pharmaceutical Research, vol. 13: 1595–1613, Nov. 1996.*

* cited by examiner

Primary Examiner—Karen M. Hauda
Assistant Examiner—Anne Marie S. Beckerleg
(74) Attorney, Agent, or Firm—Benjamin Aaron Adler

(57) ABSTRACT

A gene delivery vector used to generate genetically modified dendritic cells and B-cells central to the immune system. As a result, genetic modification of cells bearing the CD40 target antigen on its surface can be used to modulate immunity. Previously, both dendritic cells and B-cells have been resistant to gene transfer. The present invention serves to mediate dramatic enhancements in gene transfer to these cell types. Simultaneous with gene transfer, the vector system described herein matures dendritic cells and B-cells to a more potent immunoregulatory status. This invention provides technology for genetic manipulation of dendritic cells and B-cells.

6 Claims, 12 Drawing Sheets

IMMUNOMODULATION BY GENETIC MODIFICATION OF DENDRITIC CELLS AND B CELLS

CROSS REFERENCE TO RELATED APPLICATION

This application claims benefit of priority under 35 USC §119(e) of U.S. provisional application 60/102,257, filed Sep. 29, 1998, now abandoned.

FEDERAL FUNDING LEGEND

This invention was produced in part using funds through grant CA74242 from the National Institutes of Health. Consequently, the federal government has certain rights in this invention.

BACKGROUND OF THE INVENTION

1. Field of the Invention

The present invention relates generally to immunology and adenoviral gene therapy. More specifically, the present invention relates to immunomodulation by genetic modification of dendritic cells and B-cells.

2. Description of the Related Art

An expanding body of evidence suggests that dendritic cells (DC) play a pivotal role in the immune system [Bancheareau, J. and R. M. Steinman. 1998, Dendritic cells and the control of immunity. *Nature.* 392:2459]. Foremost, dendritic cells are recognized to serve as a key mediator of T-cell based immunity. Stemming from their important function, dendritic cells have been proposed for utility in a number of clinical strategies, especially vaccinations. It has become clear that genetic modification of these cells can promote immunity against pathogenic entities, both infectious and tumorigenic [Reeves, M. E., et al. 1996. Retroviral transduction of human dendritic cells with a tumor-associated antigen gene. *Cancer Res.* 56:5672–7]. Importantly, all of these strategies are predicated upon efficient vectors for gene delivery to dendritic cells. To this end, a number of approaches have been utilized, albeit generally with poor efficiency of gene transfer [Arthur, J. F., et al. 1997. A comparison of gene transfer methods in human dendritic cells. *Cancer Gene Ther.* 4:17–25; Van Tendeloo, V. F. I., et al. 1998. Nonviral transfection of distinct types of human dendritic cells: high-efficiency gene transfer by electroporation into hematopoetic progenitor- but not monocyte-derived dendritic cells. *Gene Ther.* 5:700–7]. One candidate has been replication defective adenoviral vector. This vector has been suggested to be well suited for clinical applications by virtue of its high titer, efficiency gene delivery and exhuberant gene expression.

In spite of these theoretical advantages, the relative resistance of dendritic cells to adenoviral vector infection has confounded obtaining the full benefit of gene based immunotherapy strategies. [Arthur, J. F., et al. 1997. A comparison of gene transfer methods in human dendritic cells. *Cancer Gene Ther.* 4:17–25; Dietz, A. B. and S. Vuk-Pavlovic. 1998. High efficiency adenovirus-mediated gene transfer to human dendritic cells. *Blood.* 91:392–8]. The phenomenon of dendritic cell resistance to adenoviral mediated gene transfer may be based upon the paucity of adenoviral entry receptors. In permissive cells, the projecting adenoviral fiber-knob protein mediates binding to the cell surface coxsackie-adenovirus receptor (CAR) followed by interaction with and internalization of the virion by either of the av integrins avb3 or avb5 [Wickham, T. J., et al. 1993. Integrins $\alpha v \beta 3$ and $\alpha v \beta 5$ promote adenovirus internalization but not virus attachment. 73:309–19; Bergelson, J. M., et al. 1997. Isolation of a common receptor for Coxsackie B viruses and adenoviruses 2 and 5, *Science.* 275:1320–3]. The present analysis has revealed an absence of CAR but adequate expression of the av integrin, $\alpha v \beta 5$. High efficiency gene transfer independent of CAR expression by means of adenovirus targeted by bispecific entities to alternate cellular receptors has previously been shown [Douglas, J. T., et al. 1996. Targeted gene delivery by tropism modified adenoviral vectors. *Nature Biotech.* 14:1574–8]. It was postulated that a similar strategy targeting the marker CD40, expressed on dendritic cells, might enhance gene transfer to dendritic cells.

A bispecific antibody was generated through chemical conjugation of a neutralizing anti-fiber-knob monoclonal antibody to a monoclonal antibody with affinity for the dendritic cell receptor, CD40. The present invention demonstrates that adenovirus complexed with this bispecific entity mediates dramatic enhancements in gene transfer to monocyte derived dendritic cells. More importantly, an upregulation of several dendritic cell maturational markers and enhanced allo-MLR performance after infection with CD40-targeted vector was observed, indicating the vector itself possesses maturational properties.

Thus, the prior art is deficient in methods of transducing dendritic cells and B-cells for immunomodulatory purposes. The present invention fulfills this long-standing need and desire in the art.

SUMMARY OF THE INVENTION

A bispecific antibody was generated through chemical conjugation of antibodies with affinities for the adenovirus fiber-knob and a dendritic cell receptor, CD40. The present invention shows that CD40 targeted adenovirus mediates dramatic enhancements in gene transfer to monocyte derived dendritic cells and that these enhancements can be attributed to a quantitative increase in the number of cells transduced. Additionally, the present invention shows that this enhancement is specific to the epitope recognized by the G28.5 antibody through successful blockade with the parent monoclonal, G28.5, and failure of the conjugate to mediate gene transfer on CD40 negative lines. Furthermore, an upregulation of several well documented dendritic cell maturational markers and enhanced allo-MLR by these cells was observed after infection with a retargeted vector. The dual role of CD40 in this scenario as both a surrogate adenovirus receptor and a powerful trigger of dendritic cell maturation may prove fortuitous as a retargeting strategy to this critical cell type of the immune system.

One object of the present invention is to provide a n adenovirus vector capable of targeting and transducing immune system cells, such as dendritic cells and B-cells, wherein transduction of B-cells results in maturation of the B-cells.

In an embodiment of the present invention, there is provided an immunomodulatory adenovirus, comprising: an adenoviral vector, and a bispecific antibody, comprising an antibody, or fragment thereof, recognizing a fiber-knob protein of said adenovirus conjugated to an antibody, or fragment thereof, recognizing a CD40 antigen, wherein said adenovirus is targeted to and transduces immune system cells resulting in modulation of said cells. Additionally, the bispecific antibody may be the product of a gene fusion.

In yet another embodiment, there is provided a n immunomodulatory adenovirus, comprising: a recombinant adenoviral vector, wherein the adenoviral gene encoding a fiber-knob protein has been replaced with a gene encoding an antibody, or fragment thereof, recognizing a CD40 antigen, or encoding the natural ligand of CD40, the trimeric CD40 ligand. When the adenovirus is targeted to and transduces immune system cells, the transduction results in modulation of the cells.

In yet another embodiment of the present invention, the adenoviral vector may express a therapeutic gene, selected from the group consisting of a gene encoding a tumor antigen, a gene encoding an antigen for an infectious agent, a gene encoding a cytotoxic agent and a gene encoding an immunomodulatory agent; the antibody recognizing the CD40 antigen is G28.5; the immune system cells are selected from the group consisting of dendritic cells and B-cells, as well as non-immune cells selected from the group consisting of vascular endothelium cells, epithelium cells, cells exhibiting chronic inflammation and cells and vessels of Karposi's sarcoma tumors; and maturation of the immune cells is indicative of modulation of the immune cells.

In yet another embodiment, there is provided a method of immunomodulation in an individual in need of such treatment, comprising the step of: administering to the individual a n immunomodulatory adenovirus, wherein the adenovirus modulates an immune response in the individual. This modulation is due to expression of a therapeutic gene by said adenovirus, and/or maturation of immune cells. The immune system cells are selected from the group consisting of dendritic cells and B-cells, as well as non-immune cells selected from the group consisting of vascular endothelium cells, epithelium cells, cells exhibiting chronic inflammation and cells and vessels of Karposi's sarcoma tumors. Generally, the method will be useful in treating an individual having a disease such as cancer, infectious diseases, allo transplant rejection, xeno transplant rejection and autoimmunity diseases. Additionally, administration of the immunomodulatory adenovirus is selected from the group consisting of systemic, intradermal and ex vivo.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention an d therefore are not to be considered limiting in their scope.

DETAILED DESCRIPTION OF THE INVENTION

Figure 1A:
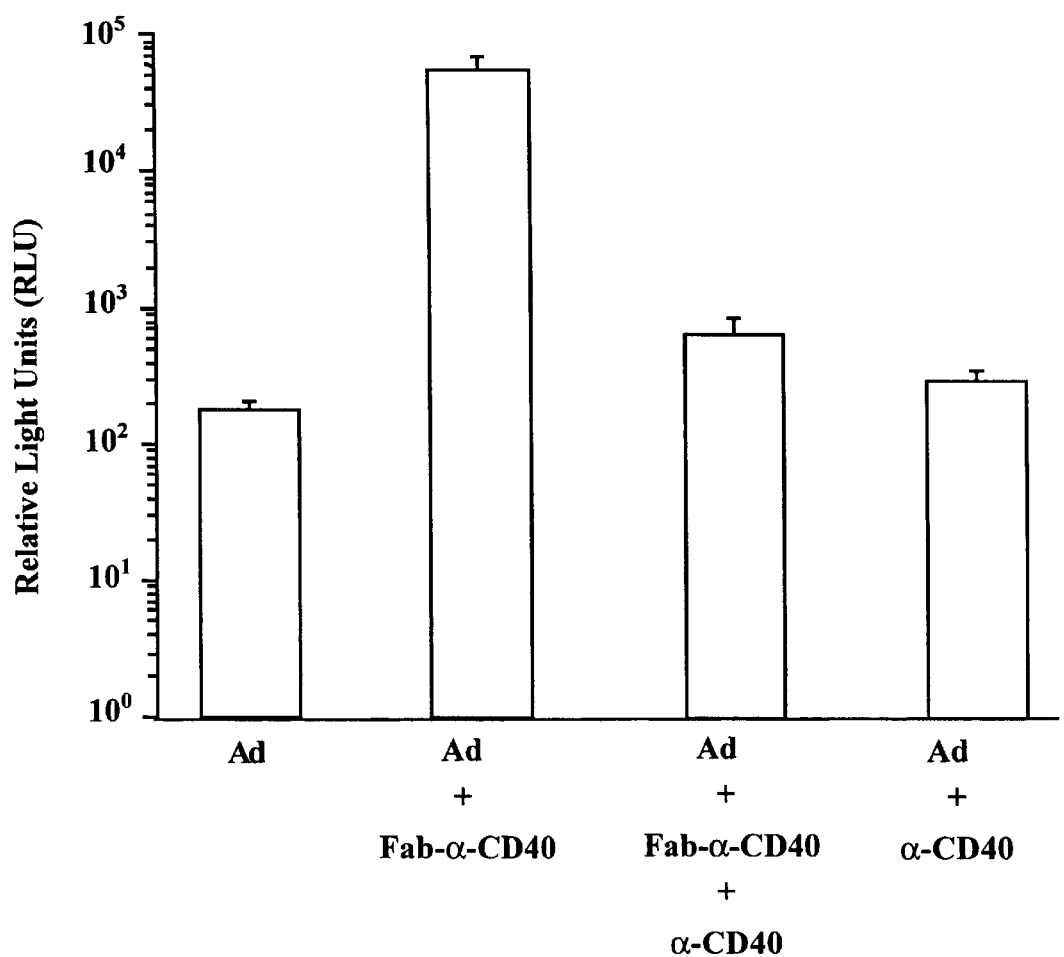
FIGS. 1A+1B shows that adenoviral targeted by Fab-anti-CD40 mediates enhanced magnitude of gene transfer that is specific for CD40. Monocyte derived dendritic cells (FIG. 1A) or the glioma cell line D65 (FIG. 1B) were preincubated in either the presence or absence of unconjugated anti-CD40 mAb were infected with AdCMVLuc either alone or complexed with Fab-anti-CD40. After 24 hour incubation, cells were assessed for expression of luciferase.
Figure 1B:
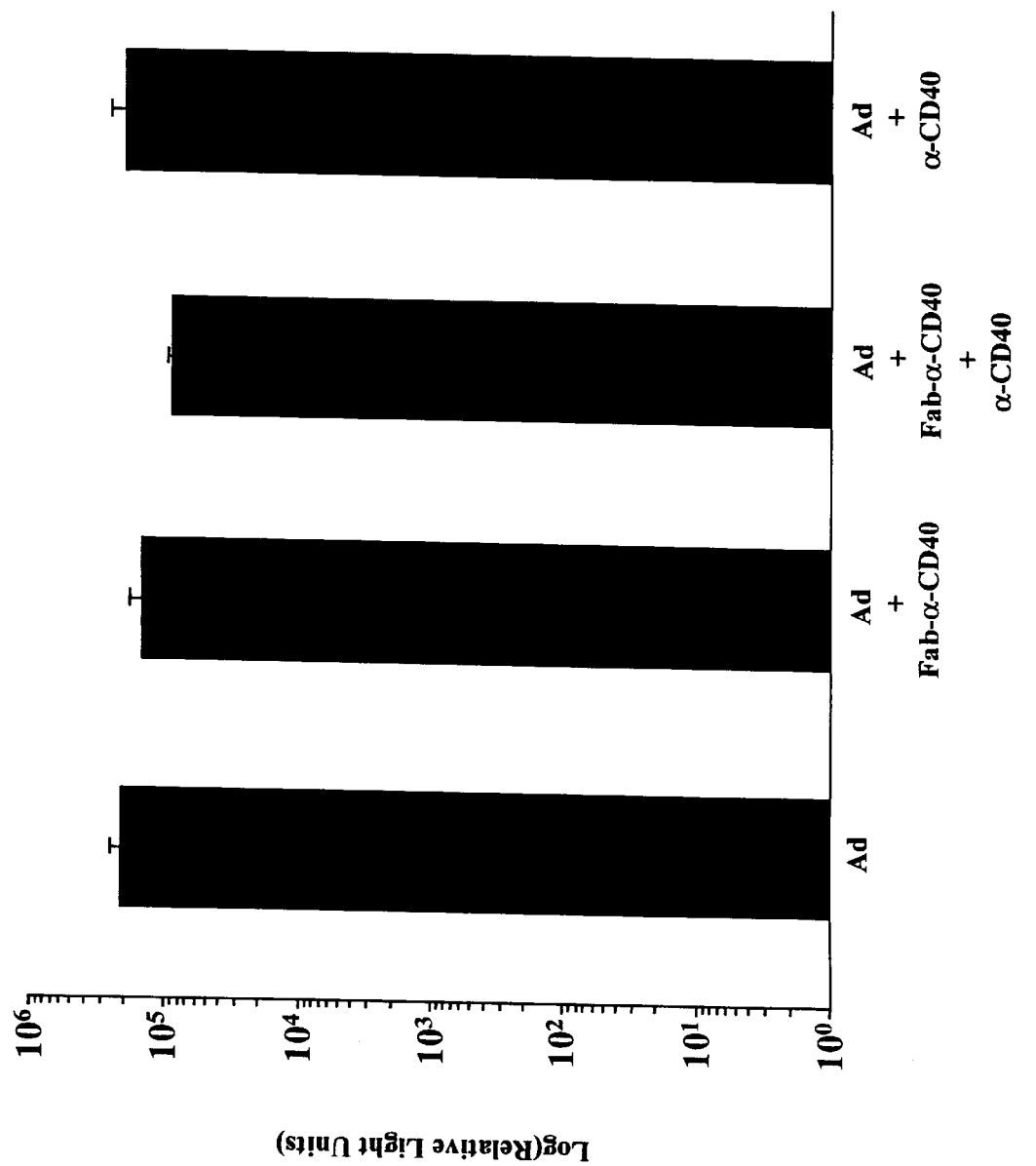
Figure 2:
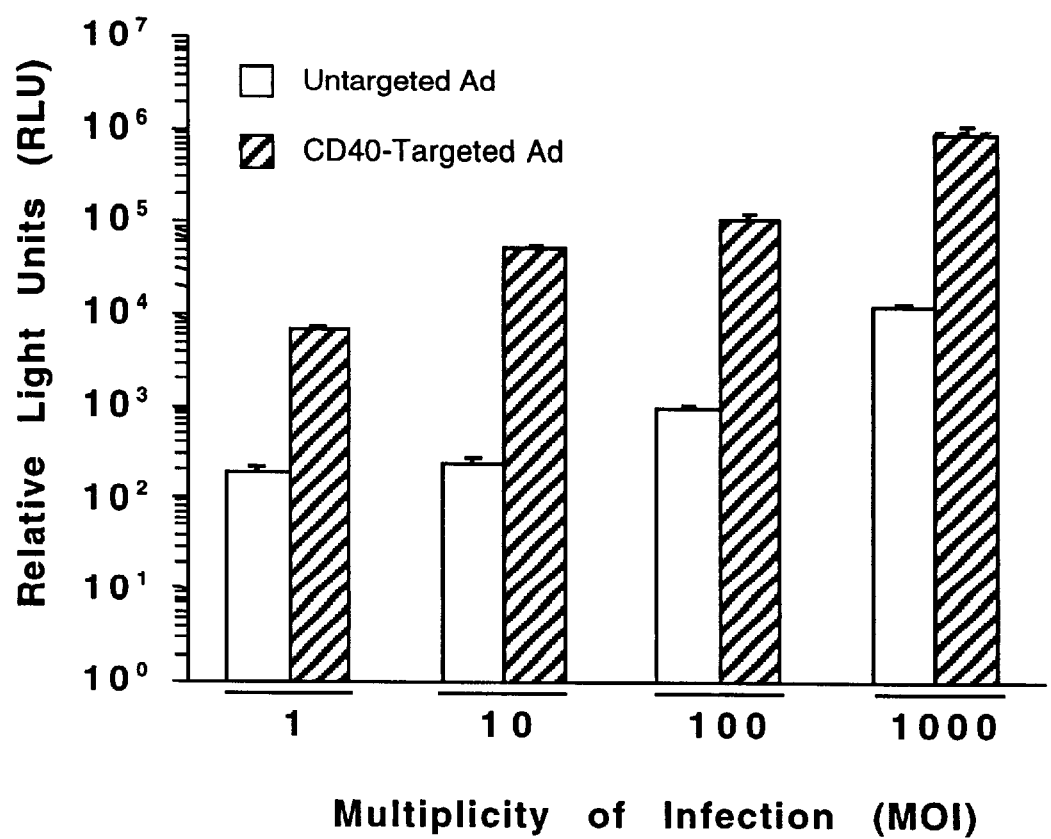
FIG. 2 shows that targeting of adenoviral to CD40 reduces the viral MOI necessary to attain a given level of gene expression. Virus, either in the presence or absence of Fab-anti-CD40 conjugate, was incubated briefly and subsequently serially diluted to correspond to Multiplicity of Infections (MOI's) of 1000, 100, 10, and 1. Monocyte derived dendritic cells were infected and cells were assayed at 24 hours for luciferase expression.
Figure 3:
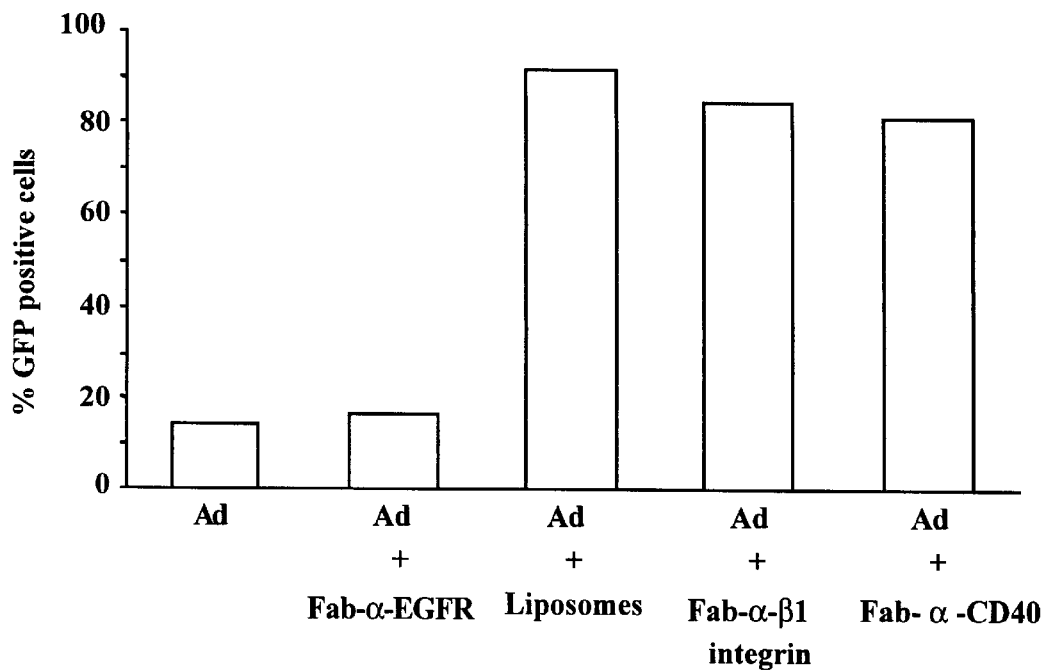
FIG. 3 shows CD40 targeted, $\beta1$ integrin targeted and liposome complexed adenoviral mediate comparable gene transfer to monocyte derived dendritic cells. Monocyte derived dendritic cells were infected with adenoviral encoding Green Fluorescent Protein (GFP) preincubated with one of the following: PBS, Fab-anti-CD40, Fab-anti-$\beta1$ integrin conjugate, Fab-anti-EGFR conjugate or Liposomes. After 24 hour incubation at 37° C., the conditions were assessed using flow cytometry for expression of GFP and are displayed as percent GFP positive cells based on analysis of 10,000 cells.
Figure 4:
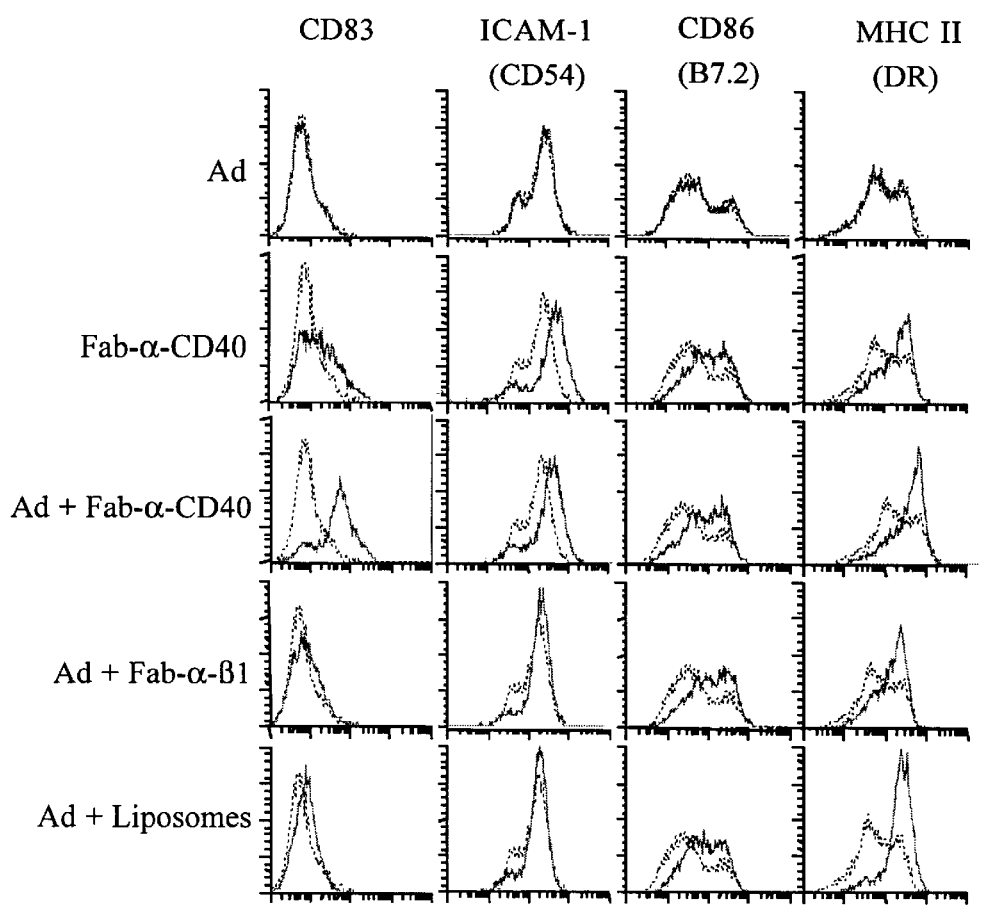
FIG. 4 shows that CD40-targeting mediates expression of dendritic cells maturational markers. Cells were treated with the indicated conditions or virus/conjugates or conjugates alone and incubated for 24 hours. Samples shown indicate expression of CD83, HLA-DR, HLA-DQ, CD86, and CD54 by flow cytometry.

A number of studies have highlighted the important consequences of genetically modified dendritic cells.

Therein, a vector to achieve efficient gene transfer to this cell type becomes paramount to many immunomodulatory strategies and yet current vector systems have struggled with low efficiency gene transfer. Adenovirus (Ad) has been used in the context of dendritic cell transduction, but its efficiency of gene delivery has proven suboptimal. By means of bispecific antibodies, the present invention successfully demonstrates enhanced gene transfer to monocyte derived dendritic cells by retargeting the adenovirus to CD40, a marker widely expressed on dendritic cells. CD40-targeted virus demonstrated both dramatic and quantitative improvements in gene transfer compared to untargeted virus. This gene transfer has been demonstrated to be specific for CD40 as illustrated by both successful blocking with the parental mAb as well as by the absence of gene transfer in CD40 negative cells. These features would be anticipated to reduce the dose of virus required for a given level of transduction and would, therefore, be expected to decrease vector related toxicity and curtail ectopic gene delivery.

Fundamental to the novelty of this system is the capacity of the vector itself to modulate the immunological status of the monocyte derived dendritic cells. This vector induces dendritic cell maturation as demonstrated phenotypically by increased expression of CD83, MHC, and costimulatory molecules as well as functionally by an enhanced allostimulatory capacity in a Mixed Lymphocyte Reaction (MLR). In comparing this vector to other adenoviral based gene transfer vectors, it has become apparent that the profound effects observed on dendritic cells are specific to CD40. This approach may serve not only as a high efficiency gene transfer vector, but may also obviate the need for supplemental steps to promote dendritic cell maturation subsequent to gene delivery.

The present invention is directed towards adenoviral vectors targeted for the CD40 cell-surface antigen of dendritic cells and B-cells. The present invention is further directed towards methods of dendritic cell and B-cell transduction using a targeted adenoviral vector. The present invention is also directed towards the method of dendritic cell and B-cell maturation following transduction with the targeted adenoviral vector of the present invention.

In accordance with the present invention, there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo; i.e., capable of replication under its own control. An "origin of replication" refers to those DNA sequences that participate in DNA synthesis. An "expression control sequence" is a DNA sequence that controls and regulates the transcription and translation of another DNA sequence. A coding sequence is "operably linked" and "under the control" of transcriptional and translational control sequences in a cell when RNA polymerase transcribes the coding sequence into mRNA, which is then translated into the protein encoded by the coding sequence.

In general, expression vectors containing promoter sequences which facilitate the efficient transcription and translation of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence. A "cDNA" is defined as copy-DNA or complementary-DNA, and is a product of a reverse transcription reaction from an mRNA transcript. An "exon" is an expressed sequence transcribed from the gene locus, whereas an "intron" is a non-expressed sequence that is from the gene locus.

Transcriptional and translational control sequences are DNA regulatory sequences, such as promoters, enhancers, polyadenylation signals, terminators, and the like, that provide for the expression of a coding sequence in a host cell. A "cis-element" is a nucleotide sequence, also termed a "consensus sequence" or "motif", that interacts with other proteins which can upregulate or downregulate expression of a specicif gene locus. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

The term "oligonucleotide" is defined as a molecule comprised of two or more deoxyribonucleotides, preferably more than three. Its exact size will depend upon many factors which, in turn, depend upon the ultimate function and use of the oligonucleotide. The term "primer" as used herein refers to a n oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

Primers are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to enzymes which cut double-stranded DNA at or near a specific nucleotide sequence.

"Recombinant DNA technology" refers to techniques for uniting two heterologous DNA molecules, usually as a result of in vitro ligation of DNAs from different organisms. Recombinant DNA molecules are commonly produced by experiments in genetic engineering. Synonymous terms include "gene splicing", "molecular cloning" and "genetic engineering". The product of these manipulations results in a "recombinant" or "recombinant molecule".

A cell has been "transformed", "transfected" or "transduced" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations. An organism, such as a plant or animal, that has been transformed with exogenous DNA is termed "transgenic".

As used herein, the term "host" is meant to include not only prokaryotes but also eukaryotes such as yeast, plant and animal cells. A recombinant DNA molecule or gene can be used to transform a host using any of the techniques commonly known to those of ordinary skill in the art. One preferred embodiment is the use of a vectors for purposes of prokaryotic transformation. Prokaryotic hosts may include *E. coli, S. tymphimurium, Serratia marcescens* and *Bacillus subtilis*. Eukaryotic hosts include yeasts such as *Pichia pastoris*, mammalian cells and insect cells, and more preferentially, plant cells, such as *Arabidopsis thaliana* and *Tobaccum nicotiana*.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, the coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

As used herein, "fragment," as applied to a antibody, will ordinarily be at least 10 residues, more typically at least 20 residues, and preferably at least 30 (e.g., 50) residues in length, but less than the entire, intact sequence. Antibody fragments can be generated by methods known to those skilled in the art, e.g., by enzymatic digestion of naturally occurring or recombinant antibodies, by recombinant DNA techniques using an expression vector that encodes a defined fragment of an antibody, or by chemical synthesis. The ability of a candidate fragment to exhibit binding to an antigen can be assessed by methods described herein.

A standard Northern blot assay can be used to ascertain the relative amounts of mRNA in a cell or tissue obtained from plant or other transgenic tissue, in accordance with conventional Northern hybridization techniques known to those persons of ordinary skill in the art. Alternatively, a standard Southern blot assay may be used to confirm the presence and the copy number of a gene in transgenic systems, in accordance with conventional Southern hybridization techniques known to those of ordinary skill in the art. Both the Northern blot and Southern blot use a hybridization probe, e.g. radiolabelled cDNA, or a fragment of that DNA sequence at least 20 (preferably at least 30, more preferably at least 50, and most preferably at least 100 consecutive nucleotides in length). The DNA hybridization probe can be labelled by any of the many different methods known to those skilled in this art.

The labels most commonly employed for these studies are radioactive elements, enzymes, chemicals which fluoresce when exposed to untraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase.

U.S. Pat. Nos. 3,654,090, 3,850,752, and 4,016,043 are referred to by way of example for their disclosure of alternate labeling material and methods.

As used herein, the term immunomodulatory shall refer to the capacity to promote or suppress immunity towards cancer, infectious agents, autoimmune antigens, or allo/xeno transplants.

As used herein, the term maturation, as it refers to immune system cells, refers to expression of specific surface markers, production of defined soluble factors, or enhanced performance in a Mixed Lymphocyte Reaction all of which are known to be characteristic of a cell which has become more efficient in the capacity to elicit a response from effector cells, such as T-cells.

As used herein, the term "CD40 antigen" shall refer to a member of the TNF receptor (TNFR) family. It serves as the receptor for CD40 Ligand (gp39). This molecule is known to be expressed on B-lymphocytes, monocytes, dendritic cells, endothelium, epithelial cells, and fibroblasts. Of note, this molecule is known to be especially prevalent in areas of activated endothelium (such as chronic inflammation) and on the vessels of Kaposi's sarcoma.

It is specifically contemplated that pharmaceutical compositions may be prepared using the novel adenoviral vector of the present invention. In such a case, the pharmaceutical composition comprises the novel adenoviral vector of the present invention and a pharmaceutically acceptable carrier. A person having ordinary skill in this art would readily be able to determine, without undue experimentation, the appropriate dosages and routes of administration of this adenoviral vector of the present invention. When used in vivo for therapy, the adenoviral vector of the present invention is administered to the patient or an animal in therapeutically effective amounts, i.e., amounts that eliminate or reduce the tumor burden due to an immunomodulatory effect. It will normally be administered parenterally, preferably intravenously, but other routes of administration will be used as appropriate. The dose and dosage regimen will depend upon the nature of the disease and its population, the characteristics of the particular vector, e.g., its therapeutic index, the patient, the patient's history and other factors. The amount of adenoviral vector of the present invention administered will typically be in the range of about 0.001 to about 500 mg/kg of patient weight. The schedule will be continued to optimize effectiveness while balanced against negative effects of treatment. See Remington's Pharmaceutical Science, 17th Ed. (1990) Mark Publishing Co., Easton, Pa.; and *Goodman and Gilman's: The Pharmacological Basis of Therapeutics* 8th Ed (1990) Pergamon Press.

For parenteral administration, the adenoviral vector will most typically be formulated in a unit dosage injectable form (solution, suspension, emulsion) in association with a pharmaceutically acceptable parenteral vehicle. Such vehicles are preferably non-toxic and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. The adenoviral vector will typically be formulated in such vehicles at concentrations of about 0.001 mg/ml to 500 mg/ml.

Thus, the present invention is directed to a gene delivery system for the genetic manipulation of immune system cells, comprising: (a) an adenovirus; and (b) a component recognizing CD40 antigen. Preferably, the component recognizing the CD40 antigen is selected from the group consisting of a trimeric CD40 ligand conjugated to a fiber-knob protein of the adenovirus and a first antibody, or fragment thereof, directed to a fiber-knob protein of said adenovirus, wherein said first antibody is attached to a second antibody, or fragment thereof, directed to CD40 antigen. A representative antibody directed to CD40 antigen is G28.5.

In one aspect, the first antibody and second antibody may be genetically fused together. This gene delivery system can be used to transduce and immunomodulate immune system cells. Furthermore, this system may also comprise a therapeutic gene. Representative therapeutic gene include a gene encoding a tumor antigen, a gene encoding an antigen for an infectious agent, a gene encoding an autoimmune antigen, an immunomodulatory gene and a gene encoding a cytotoxic agent. Representative immune system cells which can be transduced and immunomodulated using this system include of dendritic cells and B-cells. In one aspect, the B-cells are matured following contact with said system.

The present invention is also directed to a method of genetically manipulating immune system cells in an individual in need of such treatment, comprising the step of administering the gene delivery system described above to the individual. This method may be useful where the individual has a disease selected from the group consisting of cancer, an infectious disease, allotransplant rejection, xenotransplant rejection and autoimmune diseases. Representative immune system cells which can be transduced and immunomodulated using this system include of dendritic cells and B-cells. In one aspect, the B-cells are matured following contact with said system.

The present invention is also directed to a method of genetically manipulating immune system cells in an individual in need of such treatment, comprising the step of administering the gene delivery system comprising a therapeutic gene to said individual.

The present invention is also directed to a recombinant adenoviral vector for the genetic manipulation of immune system cells, wherein the adenoviral gene encoding a fiber-knob protein has been replaced with a gene encoding a protein recognizing a CD40 antigen. Preferably, the gene recognizing said CD40 antigen is selected from the group consisting of a gene encoding a trimeric CD40 ligand and a gene encoding an antibody, or fragment thereof, directed to said CD40 antigen. A preferred antibody directed to CD40 antigen is G28.5. This recombinant adenoviral vector can be used to transduce and immunomodulate immune system cells. The recombinant adenoviral vector may further comprise a therapeutic gene such as a gene encoding a tumor antigen, a gene encoding a n antigen for an infectious agent, a gene encoding an autoimmune antigen, an immunomodulatory gene and a gene encoding a cytotoxic agent. This recombinant adenoviral vector can be used in a method of genetic manipulating immune system cells in an individual in need of such treatment. Such individuals may have a disease such a s cancer, an infectious disease, allo transplant rejection, xeno transplant rejection and autoimmune diseases.

The following examples are given for the purpose of illustrating various embodiments of the invention and are not meant to limit the present invention in any fashion:

EXAMPLE 1
Culture of Monocyte-Derived Dendritic Cells (MoDC)

Peripheral Blood Mononuclear Cells (PBMC) were isolated from heparinized peripheral blood by density cetrifugation over Lymphoprep (Nycomed AS, Oslo, Norway) and cryopreserved in RPMI 1640 medium supplemented with 12.5% DMSO and 25% FCS, which has previously been described as the optimal cryopreservative medium for monocyte derived dendritic cells and their precursors (Makino and Baba). Fresh or cryopreserved PBMC were suspended at a concentration of 3 to 5 million cells per ml in Iscove's modified Dulbecco's medium containing 50 U/mL penicillin-streptomycin, 1.6 mM L-Glutamine, 0.01 mM β-mercaptoethanol (complete medium), and 10% FCS and were allowed to adhere to the bottom of plastic culture flasks (NUNC, Intermed, Denmark). After 2 hours at 37° C., non-adherent cells were removed by rinsing with PBS. The adherent cells were cultured for a further 6 days in complete medium with 10% FCS supplemented with 1000 U/ml rIL-4 (CLB, Amsterdam, The Netherlands) and 100 ng/mL GM-CSF. Loosely adherent cells with typical dendritic cell morphology were harvested (adherent cells were detached by incubation with 0.5 mM EDTA in PBS) and used for FACS analysis or adenovirus mediated gene transfer.

EXAMPLE 2
Mixed Lymphocyte Reaction

For allogeneic and autologous Mixed Lymphocyte Reaction, monocyte derived dendritic cells were added as stimulator cells to roundbottom 96-well culture plates (Nunclon Delta, Intermed, Denmark) at graded doses. Non-adherent lymphocyte fractions were used as a source for responder cells. Per well 1×10$^5$ lymphocytes were added to the allogeneic or autologous monocyte derived dendritic cells at the indicated Responder/Stimulator ratios (R:S). The cells were cultured for 3 days in complete medium with 10% Human Pooled Serum (CLB, Amsterdam, The Netherlands). During the last 18 hours, [$^3$H]-thymidine was added (0.4 mCi per well) (Amersham, Aylesbury, UK), after which the cells were harvested onto fiberglass filters and [$^3$H]-thymidine incorporation was determined using a flatbed liquid scintillation counter (Wallac, Turku, Finland).

EXAMPLE 3
Phenotypic Analyses

Cell staining was performed using monoclonal antibodies (MoAbs) directly conjugated to Fluorescein Isothiocyanate (FITC) or to Phycoerthrin (PE). The antibodies used were HB15 (CD83), BL6 (CD1a), BU15 (CD11c), MAB89 (CD40), (Immunotech, Marseille, France), SK7 (CD3), 4G7 (CD19), B73.1 (CD16), MoP9 (CD14), NCAM 16.2 (CD56), L243 (HLA-DR), 2A3 (CD25) (Becton Dickinson, San Jose, Calif.), 2331 (CD86), G46-2.6 (HLA A, B, C), HA58 (CD54), and TU169 (HLA-DQ) (Pharmingen, San Diego, Calif.). The samples were analyzed on a FACStar using Cellquest FACS analysis software (Becton Dickinson).

When cells were infected with adenoviral prior to analysis, all values for conjugate or virus used in microscale luciferase assays were proportionately increased for the larger number of cells to be infected. Cells were infected in batches of 1 million cells using AdCMVLuc. Cells were infected in a similar manner to that used for luciferase gene transfer analysis, with the only exception that cells were left in microcentrifuge tubes for the entire 24 hour incubation after washing and addition of complete medium. At 24 hours, the cells were assessed by flow cytometry for expression of maturation associated surface markers.

EXAMPLE 4
Viruses and Cell Lines

AdCMVLuc, a first generation E1-, E3-deleted vector expressing firefly luciferase from the CMV immediate early promoter, was obtained from Robert Gerard (University of Leuven, Leuven, Belgium). Viruses were propagated and plaque titered on the permissive line 293 and purified by double centrifugation on CsCl gradients. All virus aliquots were stored at −80° C. until use. Murine monoclonal antibody RmcB to human coxsackie/adenovirus receptor (from Dr. Robert Finberg, Dana Farber Cancer Institute) has been described previously. Murine monoclonal antibody LM609 to avb3 and P1F6 to avb5 integrin were purchased from Chemicon (Temecula, Calif.) and Gibco BRL (Gaithersburg, Md.) respectively. The neutralizing murine monoclonal antibody 1D6.14 specific for the carboxy-terminal, receptor binding domain of adenoviral serotype 5 has been described. The hybridomas G28.5, producing anti-CD40 monoclonal antibodies (ATCC#:9110-HB) and TS2/16.2.1 (ATCC#: 243-HB; "TS2") producing monoclonal antibodies against the β1 integrin, were purchased from ATCC. Both hybridomas were used to generate ascites in SCID mice.

Antibodies were purified on an FPLC chromatography system using HiTrap Protein A column (Pharmacia) and the MAPS binding buffer system (Bio-Rad). The 1D6.14 monoclonal was digested to a Fab fragment using immobilized papain (Pierce) and fragments were purified by negative selection of Fc fragments using HiTrap Protein A columns.

EXAMPLE 5
Antibodies and Conjugates

Both 1D6.14-Fab and monoclonal antibodies G28.5 and TS2 were concentrated to 10 mg/mL in Borate Buffer. Chemical conjugation of the Fab to mAb in a 1:1 molar ratio was performed as described [Segal, D. M. and B. J. E. G. Bast. 1994. Production of bispecific antibodies. Editors: Coligan, J. E., A. M. Kruisbeek, D. A. Marguiles, E. M. Shevach, W. Strober. Current Protocols in Immunology. John Wiley and Sons, New York. Volume 1. Sections 2.13.1–2.13.16]. Conjugate was purified on a HR 10/30 Superose 12 column using FPLC (Pharmacia, Piscataway, N.J.) in Borate buffer pH 8.5, wherein the fractions were pooled that corresponding to a 1:1 ratio of anti-receptor antibody to Fab, at an approximate molecular weight of 200 kDa.

EXAMPLE 6
Protocol for Ad Infection and Luciferase Analysis

Nonadherent monocyte derived dendritic cells were collected and mixed with the 0.5 mM EDTA released adherent cell fraction followed by washing in complete RPMI containing 2.5% FCS. Twenty-four thousand cells in a volume of 50 μl were distributed to individual microcentrifuge tubes in triplicate for each test condition. The use of microcentrifuge tubes enabled simplified infection and washing of cells, which represented both adherent and nonadherent fractions. Conjugate and virus were incubated for 30 minutes at room temperature in a minimal volume of under 10 μl per each test condition's worth of virus. Following incubation the mixture was diluted such that 100 μL was used to infect each microcentrifuge tube of cells. The amount of virus in this volume corresponded to a multiplicity of infection of 100. Microcentrifuge tubes containing the infection mixture were placed at 37° C. for 1 hour. Subsequently, to remove unbound virus, cells were washed in the tubes with PBS, centrifuged, and the supernatant aspirated. Pelleted cells were resuspended in 1 mL of RPMI 10% FCS and moved to individual wells of a polylysine coated 24-well plate for overnight incubation. Use of polylysine coated wells enabled simpler processing in subsequent luciferase assays by anchoring of both adherent and suspension fractions to the well surface. Following 24 hours of incubation post infection, supernatant was aspirated from all wells and the cells were processed using the Promega Luciferase Assay Kit. Briefly, cells were lysed directly on the plate and subjected to one freeze thaw cycle. The lysates were analyzed by mixture with luciferase substrate and immediate evaluation on a Lumat luminometer.

For blocking experiments, cells were blocked with the parental (unconjugated) G28.5 monoclonal prior to infection. Due to the rapid internalization kinetics previously reported for this monoclonal, all blocking was performed at 4° C. to minimize receptor modulation from the cell surface. After 30 min of incubating cells with the blocking agent, virus complexed with the optimal amount of Fab-G28.5 was added directly to the cells and incubated further for a period of 30 min before washing and transition to the 24-well plate at 37° C. For blocking with Fab, virus was preincubated with an excess of a previously determined neutralizing concentration of 1D6.14 Fab. In this regard, Fab was merely susbstituted in place of conjugate for the indicated conditions.

EXAMPLE 7
Conjugate Titration to Ascertain the Optimal Amount of Conjugate for Retargeting To determine the amount of retargeting conjugate necessary to optimally coat an adenovirus, the conjugate was titrated on a predetermined number of viral particles at an MOI of 100, wherein gene transfer was measured in terms of luciferase expression as relative light units, RLU, in monocyte derived dendritic cells. Monocyte derived dendritic cells were infected with AdCMVLuc preincubated with increasing concentrations of Fab-G28.5. Further increases in the conjugate:virus ratio proved to reduce the magnitude of retargeted gene transfer, presumably stemming from competition for CD40 binding by excess Fab-G28.5 conjugate. This titration tested given masses of conjugate ranging from 0.01 ng to 2000 ng/well with intervals at every half $\log^{10}$ of mass following incubation with $2.4 \times 10^6$ virions. The mass of conjugate corresponding to the highest levels of luciferase gene expression was termed an "optimal dose" and was used in all subsequent experiments.

EXAMPLE 8
GFP Reporter Gene to Demonstrate Quantitative Gene Transfer

To ensure that the gene transfer observed with luciferase correlated to an actual increased number of cells transduced, cells were also infected with adenoviral carrying the gene for GFP. As for cells undergoing flow cytometry based marker analysis, monocyte derived dendritic cells were batch infected using AdGFP complexed to the optimal ratio of Fab-G28.5 conjugate. Twenty-four hours post-infection, positive cells were visualized using flow cytometry.

EXAMPLE 9
Analysis of Differential MOI Between CD40-Targeted and Untargeted Ad Cells were batch infected with different MOI's of CD40-targeted and untargeted virus. Fab-G28.5 was complexed with AdCMVLuc at a concentration corresponding to 1000 MOI. Subsequently, this mixture was serially diluted to MOI's of 500, 100, 50, 10, and 1. Simultaneously, samples of the same MOI's of adenovirus without retargeting conjugate were prepared for comparison with targeted samples. Monocyte derived dendritic cells were then infected and analyzed for luciferase as was done in the luciferase gene transfer experiments.

EXAMPLE 10
Validation of Monocyte Derived Dendritic Cells

Monocyte derived dendritic cells were generated by treatment of monocytes isolated from peripheral blood with IL-4 and GM-CSF. The identity of these cells was validated in two ways. Purity was demonstrated through flow cytometry for lack of expression of CD14, CD3 and CD19. Further, the cells exhibited a dendritic cell phenotype with some veiled cells and a mixture of adherent and nonadherent fractions associated in multicellular clusters. These monocyte derived dendritic cells were negative for expression of dendritic cells maturational markers, such as CD83, and were thus immature.

EXAMPLE 11
Observed Enhancement in Gene Transfer is Specific to CD40

To determine the amount of retargeting conjugate necessary to optimally coat an adenovirus, the conjugate was titrated on a predetermined number of viral particles at an MOI of 100, wherein gene transfer was measured in terms of luciferase expression in monocyte derived dendritic cells. Monocyte derived dendritic cells were infected with AdCMVLuc preincubated with increasing concentrations of Fab-G28.5. CD40-targeted gene transfer reached a maximum with a Fab-G28.5 conjugate-virus ratio of 30 ng Fab-G28.5 per $2.4 \times 10^6$ pfu ($1.75 \times 10^8$ particles/mL as determined by $OD_{260}$). Further increases in the conjugate to virus ratio proved to reduce the magnitude of retargeted gene transfer, presumably stemming from competition for CD40 binding by excess Fab-G28.5 conjugate. At the optimal ratio of conjugate to virus, CD40 targeted adenoviral demonstrated a two $\log^{10}$ enhancement in gene transfer to monocyte derived dendritic cells, as determined by expression of the Luciferase reporter gene. This optimal dose was analyzed in several ways for its specificity to CD40.

So as to implicate the anti-CD40 antibody of the conjugate as the basis for the observed enhancements in gene transfer, cells were preincubated with the parental anti-CD40 antibody, G28.5. When cells were blocked in this manner, an expected 95% reduction in retargeted gene transfer was observed. To exclude the possibility that G28.5 mAb itself was mediating enhanced adenovirus gene transfer independent of its association with the virion, cells were preincubated with unconjugated G28.5 mAb prior to infection with untargeted adenovirus. Pretreament of cells with the G28.5 monoclonal resulting in negligible enhancements in gene transfer.

To rule out the possibility that bispecific conjugate mediated nonspecific cell binding (or more specifically, by interaction of bispecific antibody with Fc receptors on dendritic cells), a n irrelevant conjugate with affinity for a marker (EGFR) absent from the surface of dendritic cells was tested. The irrelevant conjugate failed to mediate enhancements in gene transfer, further demonstrating the specificity of the observed CD40-retargeting. As a stringent test of the vector specificity, the above conditions were also tested on the CD40 negative glioma cell line, D65. The failure of adenoviral targeted by Fab-G28.5 to enhance gene expression on D65 further indicates the specificity of this vector for CD40.

EXAMPLE 12

Enhancements in Gene Transfer are Due to Quantitatively Increased Numbers of Cells Transduced While luciferase gene transfer had illustrated an overall increase in gene expression due to CD40-targeted adenovirus, the nature of this assay could indicate whether an increased number of cells had actually been transduced. To rule out the possibility that a few transduced cells were merely exhibiting more exuberant gene expression as a result of retargeting, adenovirus containing a quantitative marker, Green Fluorescent Protein, GFP, was used. The number of cells transduced was monitored through use of flow cytometry. It was determined that compared to cells infected with untargeted adenovirus, CD40-targeted adenovirus quantitatively transduced more cells. Comparable levels of gene transfer were observed with two other methods, b1 integrin targeted adenovirus and liposome complexed adenovirus. Once again, this enhanced gene transfer was absent when an irrelevant conjugate to EGFR was used.

EXAMPLE 13

Fab-G28.5 Enhances Adenovirus Mediated Gene Transfer in Different Donors and Such Retargeting Can Reduce the Viral Dose Required to Achieve a Given Level of Transgene Expression To compare the efficacy of this retargeting strategy in different donors simultaneously, CD40-targeted adenovirus was compared to untargeted adenovirus at several MOI's on monocyte derived dendritic cells. These results also indicate that at a given MOI, retargeted adenovirus yields a magnitude of gene transfer seen only in untargeted adenovirus at 100-fold higher MOI. These results highlight a significant advantage of retargeted adenovirus in that for a given level of gene transfer, significantly less infectious virions per cell are required when using a CD40 retargeted adenovirus. Since larger viral doses are associated with greater direct viral mediated cytotoxicity as well as more vigorous anti-adenovirus immune response, the potential to reduce the viral dose administered has important implications for reducing toxicities associated with use of adenovirus vectors.

EXAMPLE 14

MDCC Transduced By CD40-Targeted Ad Exhibit Phenotypic and Functional Characteristics of Mature Dendritic Cells Having demonstrated enhanced gene transfer efficacy, the effect of virus on dendritic cells as relates to their phenotypic and functional capacity was examined. To determine the effects of retargeted-adenoviral vectors or the retargeting conjugates alone on dendritic cell maturation, several markers were analyzed using flow cytometry. Cells treated 24 hours previously were analyzed for CD86, CD83, CD80, ICAM-1, MHC II (HLA-DR, HLA-DQ), and MHC I expression. While no changes in dendritic cells phenotype were observed when adenoviral was used alone, clear alterations including augmented expression of CD86, HLA-DR and HLA-DQ were observed with all three high efficiency adenoviral gene delivery systems. Unique features imparted by treatment with either Fab-anti-CD40 conjugate or CD40-targeted adenoviral included those changes most closely associated with dendritic cells maturation, namely increased expression of CD83 and ICAM-1.

Figure 6:
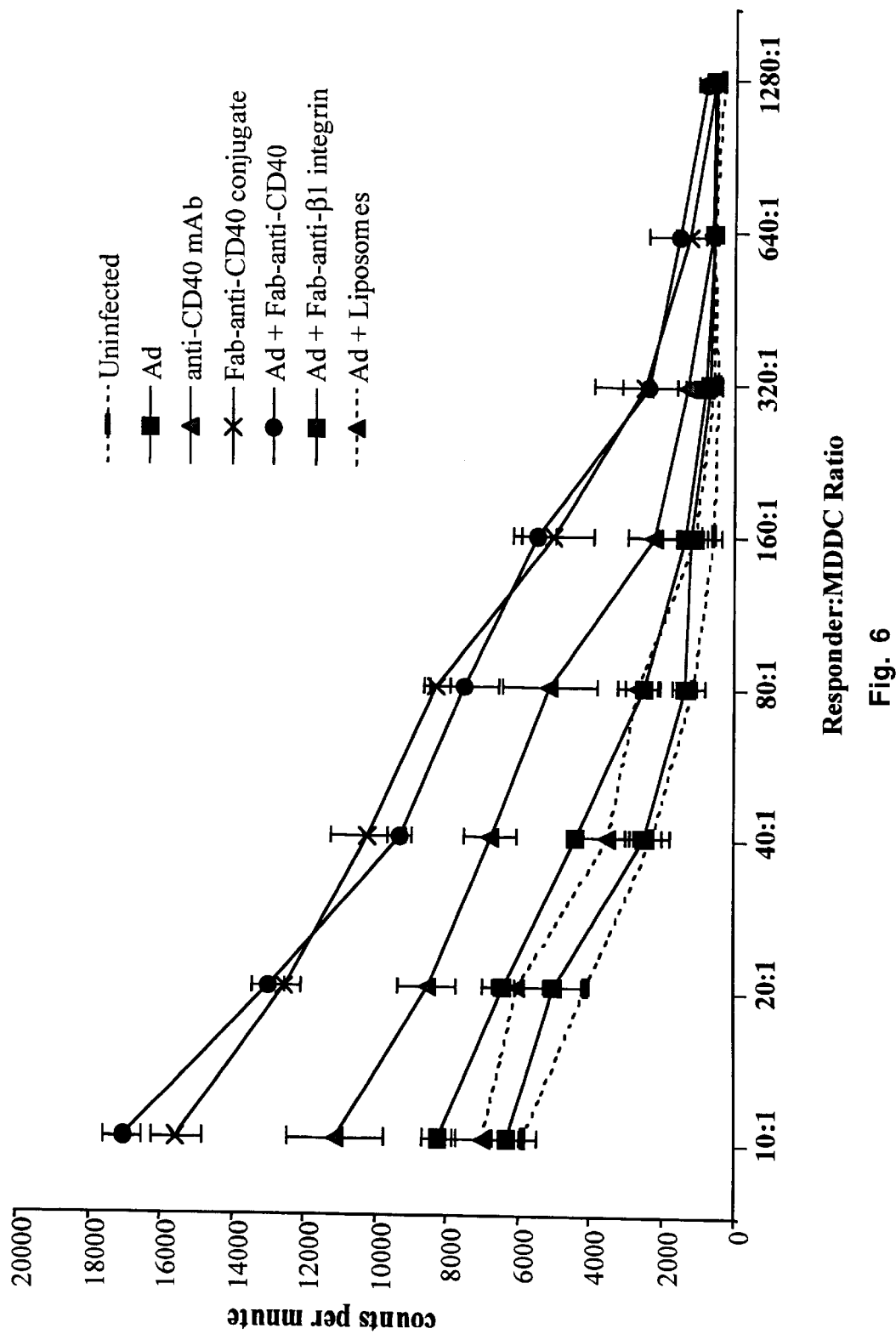
FIG. 6 shows that targeting to CD40 mediates enhancement in the capacity to generate an allo-Mixed Lymphocyte Reaction. Monocyte derived dendritic cells were treated with the indicated conditions and mixed with non-adherent lymphocyte responder cells MLR at the indicated Responder/Stimulator ratios (R:S). Cells were subsequently $^3$H labeled and assessed for cell associated cpm after 3 days.

A more rigorous index of dendritic cell maturation is the mixed lymphocyte reaction. MDDC treated using several vectors or conjugates were combined with responder cells from an allogeneic donor and tested for the capacity to elicit responder cell proliferation. While adenoviral alone did not mediate enhancement in MLR, any treatments in the presence or absence of adenoviral were able to dramatically promote MDDC reactivity in the allo-MLR (FIG. 6). Moreover, while the effect of unconjugated mAb was significantly less than that seen with Fab-anti-CD40 conjugate in the presence of adenoviral, the effect of conjugate alone was comparable to that seen with the conjugate with virus. One possible explanation of the maturational effects observed with CD40-targeting could have been a viral-mediated effect from high efficiency entry of adenoviral particles into dendritic cells. For this reason, dendritic cells infected with the alternate high efficiency adenoviral vectors β1 integrin targeted adenoviral or liposome complexed adenoviral were also tested in an MLR. The failure of these alternate vectors to mediate notable enhancements suggests the maturation phenomenon is CD40-associated.

Figure 5:
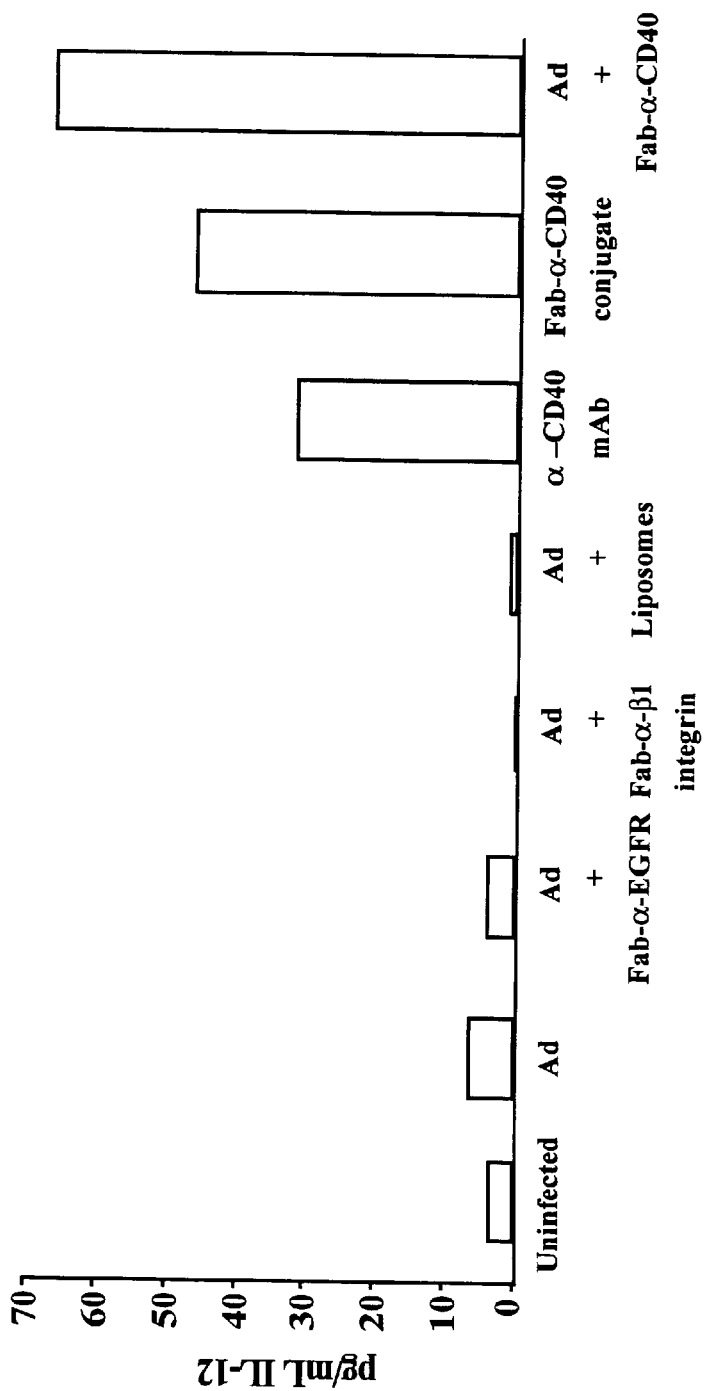
FIG. 5 shows that IL-12 production is enhanced after treatment with the anti-CD40 Ab or Fab-anti-CD40 targeting conjugate. Monocyte derived dendritic cells were treated with the indicated retargeted adenoviral or in the absence of adenoviral with unconjugated anti-CD40 Ab or the Fab-anti-CD40 conjugate. At 48 hours, the supernatants were assessed by ELISA for production of IL-12, a marker of dendritic cells maturation. Of note, values below 8 ng are beyond the linear range of detection by this assay.

As further evidence of functional maturation, MDDC supernatants were tested at 48 hours for production of IL-12, a cytokine for which expression is characteristic of dendritic cells maturation [Cella, M, et al. 1996. Ligation of CD40 on dendritic cells riggers production of high levels of IL-12 and enhances T-cell stimulatory capacity: T-T help via APC activation. J. of Exp. Med. 184:747–529] (FIG. 5). The results indicated that IL-12 levels were dramatically augmented several fold in supernatants of cells treated with unconjugated G28.5 mAb and even higher with Fab-anti-CD40 retargeting conjugate alone or with CD40-retargeted adenoviral.

Despite enormous clinical potential, widespread application of genetically modified dendritic cells has been hindered by several obstacles. Among these are the extensive handling required for ex vivo transduction, the poor gene transfer efficacy by existing vectors, and the necessity to mature dendritic cells to a immunologically potent state subsequent to gene transfer [Bancheareau, J. and R. M Steinman, 1998, Dendritic cells and the control of immunity. Nature. 392:245]. Peripheral dendritic cells's active in the process of antigen capture are referred to as "immature dendritic cells." In spite of active antigen retrieval, these cells do not express the appropriate panel of costimulatory molecules and cytokines necessary to activate effector cells such as cytotoxic T-lymphocytes (CTL's). As such, immature dendritic cells must be differentiated to an immunologically potent "mature" status by CD40 activation [Bennett, S. R. M., et al. 1998. Help for cytotoxic-T-cell responses is mediated by CD40 signaling. Nature. 393:478–480; Ridge, J. P., et al. 1998. A conditioned dendritic cell can be a temporal bridge between a CD4+ T-helper and a T-killer cell. *Nature.* 393:474–7; Schoenberger, S. P., et al. 1998. *Nature.* 393:478–80; Ridge, J. P., et al. 1998. T-cell help for cytotoxic T-lymphocytes is mediated by cd40-cd40L interactions. 393:480–3]. For this reason, the effects the CD40-targeted adenoviral vector have on the maturational status of dendritic cells was examined.

The ability of the anti-CD40 conjugate, and to a lesser extent monomeric antibody, to mediate dendritic cell maturation in the absence of virus clearly indicates that the maturation phenomenon is adenoviral-independent. Further, based on expression of CD83 and ICAM-1, production of IL-12 and improved MLR observed almost exclusively with treatment of MDDC by CD40 mAb, Fab-anti-CD40 conjugate, and CD40-targeted adenoviral but not with other adenoviral vectors tested, it seems fairly certain that this maturational phenomenon is a direct and specific result of targeting to CD40.

The present invention shows that retargeting adenoviral gene delivery to CD40 mediates dramatic increases in the magnitude of gene transfer and maturational effects that are specific for CD40. Consequently, despite the comparable enhancements of conjugate targeted adenoviral and liposome complexed adenovirus ex vivo, the more cell specific targeting and maturational potential of CD40-targeted adenoviral would, in theory, lend itself more reliably to in vivo approaches.

In sharp contrast to previous studies documenting increased CD40 expression upon dendritic cells maturation, in all cases using a CD40 mAb or CD40-based conjugate, FACS analysis revealed a reduction in surface CD40 expression at 24 hours. Since the conjugate has been detected on the cell surface at 48 hours after treatment, it is possible that the retained conjugate might have obscured subsequent detection of CD40.

The present invention shows that Fab-anti-CD40 conjugate mediates more dramatic MLR reactivity in MDDC's than seen with unconjugated anti-CD40 mAb. Previous reports implicate CD40 crosslinking as a means to activate the CD40 pathway and herein are proposed two means by which the present system has altered the crosslinking kinetics of this antibody. First, the inherent trimericity of the fiber-knob lends itself to binding of up to three conjugate molecules per each of twelve capsid vertices. Second is the semi-random nature of the chemical crosslinking procedure which can result in heterodimers with ratios besides a simple 1:1 Fab to anti-CD40 mAb.

In summary, it appears that adenovirus mediates minor effects on dendritic cells phenotype, but these effects are seen only when a sufficient number of particles enter each cell, such as by the high efficiency antibody-targeted or liposome-complexed adenoviral based gene transfer vectors. It is interesting to speculate as to whether the enhanced expression of costimulatory molecules seen with β1 integrin-targeted or liposome-complexed adenoviral is a consequence of the capsid itself entering the cell, expression of the transgene, or by background adenoviral gene expression. The dual role of CD40 in this scenario as both a surrogate adenoviral receptor and a powerful trigger of dendritic cell maturation will be useful as a retargeting strategy to this central cell type of the immune system.

One benefit of a CD40-retargeted adenoviral vector is that by delivery of an antigen-encoding gene, a larger pool of dendritic cells's can be generated with the potential to prime effector cells against the antigen of interest, especially important in the case of cryptic antigens that might otherwise be unaccessible to the immune system. Stemming from the important role of CD40 in T-helper activation of dendritic cells, such a system might also have applications in bypassing the need for CD4+ T-cell help in activation of CTL. While the utility of bispecific-antibody based targeting of adenovirus for clinical purposes has been previously suggested, the limitations of this antibody based strategy for intensive clinical applications has been recognized. For this reason, a genetic fusion strategy between the trimeric adenovirus fiber and the natural ligand of CD40, trimeric CD40L, is useful.

EXAMPLE 15

Transduction of B-Cells

Figure 7A:
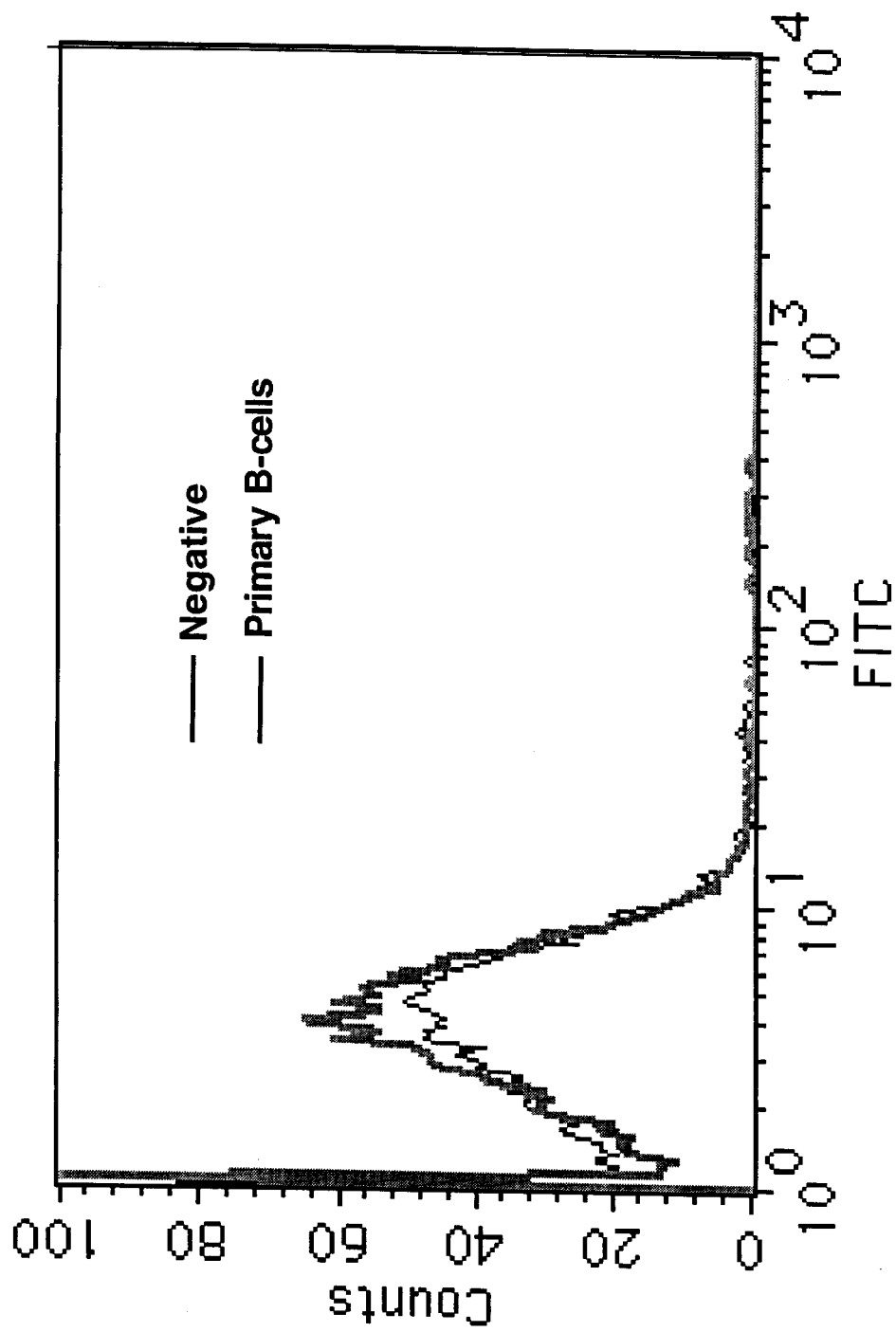
FIGS. 7A+7B shows that primary B-cells are deficient in CAR (FIG. 7A) and the $\alpha v$ integrin, $\alpha v \beta 5$ (FIG. 7B). The adenoviral entry receptors. Cells were FACS analyzed using the anti-CAR mAb RmcB and the anti-$\alpha v \beta 5$ specific mAb P1F6. (analysis of $\alpha v \beta 3$ was similar to $\alpha v \beta 5$).
Figure 7B:
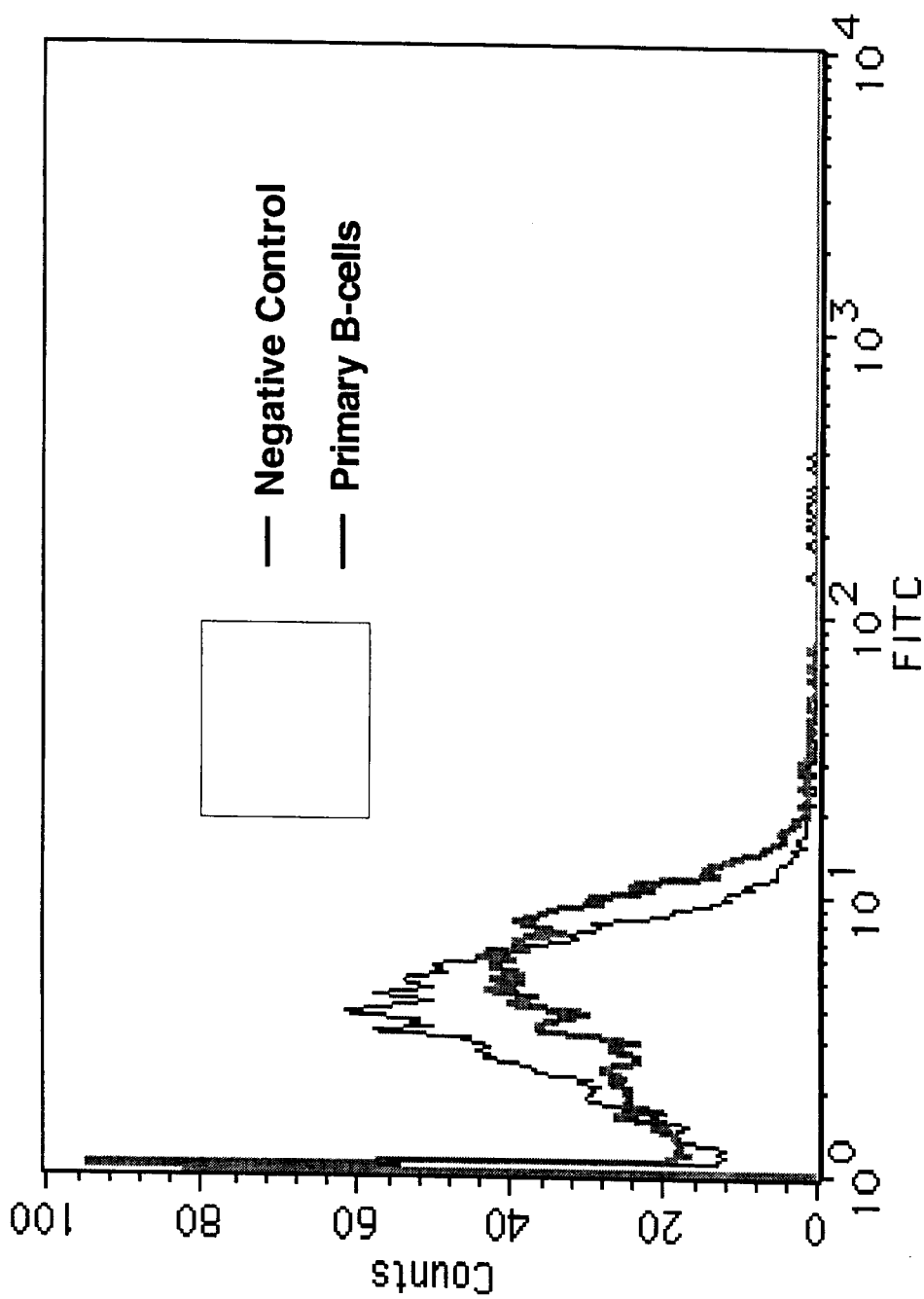

It has been recognized for quite some time that lymphocytes are a difficult cell type into which genes can be delivered. Several types of hematopoetic cells have been documented for their failure to mediate binding and/or internalization of adenoviral viral particles [Silver, L. and C. W. Anderson. 1988. Nonpermissivity of human peripheral blood lymphocytes to adenovirus type 2 infection. *J. of Virology.* 62:341–5; Mentel, R., et al. 1997. Adenovirus-receptor interaction with human lymphocytes. *J. of Med. Virology.* 51:252–7; Wattel, E., et al. 1996. Differential efficacy of adenoviral mediated gene transfer into cells from hematological cell lines and fresh hematological maligancies. *Leukemia.* 10:171–4]. A failure of primary B-cells to express both the primary adenoviral receptor CAR and the secondary receptors, the av integrins, has been recognized (FIGS. 7A & 7B). This would explain the failure of adenovirus to infect these cells effectively.

Figure 8:
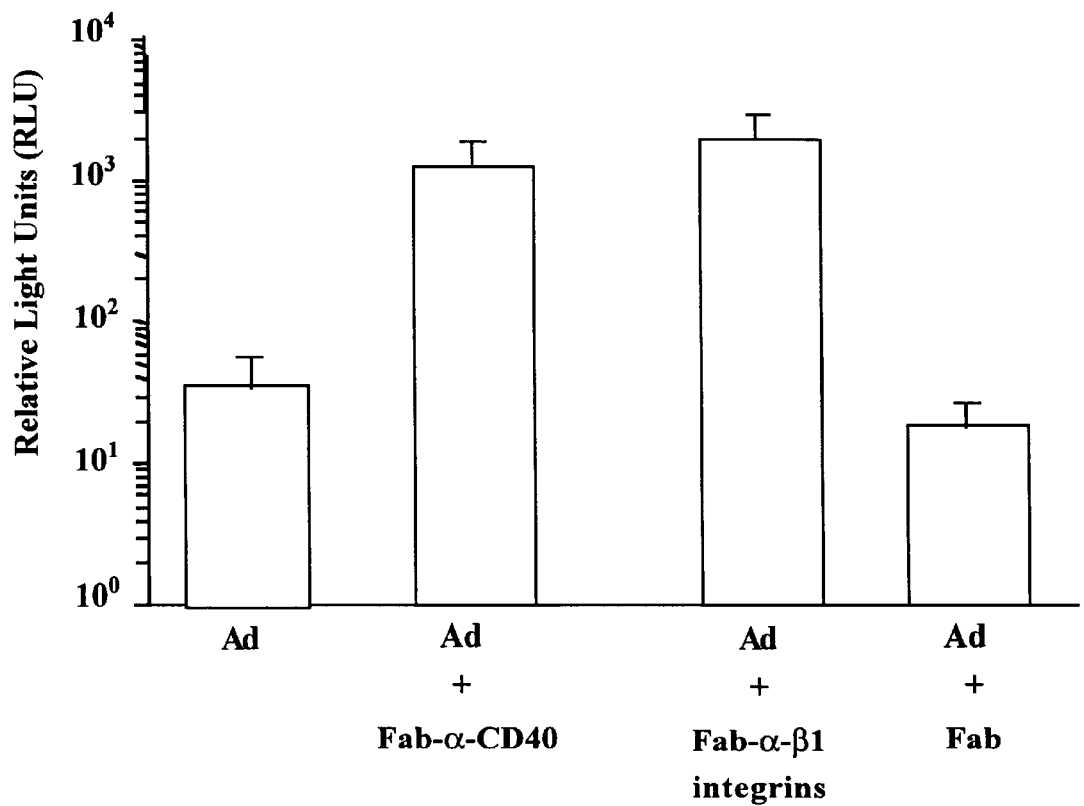
FIG. 8 shows that adenoviral targeted by Fab-anti-CD40 or Fab-anti-$\beta1$ integrins mediates enhanced magnitude of gene transfer to primary normal B-cells. Purified primary B-cells were infected with AdCMVLuc either alone or complexed the following a s indicated Fab, Fab-anti-CD40, or Fab-anti-$\beta1$ integrins. After 24 hour incubation, cells were assessed for expression of luciferase.
Figure 9:
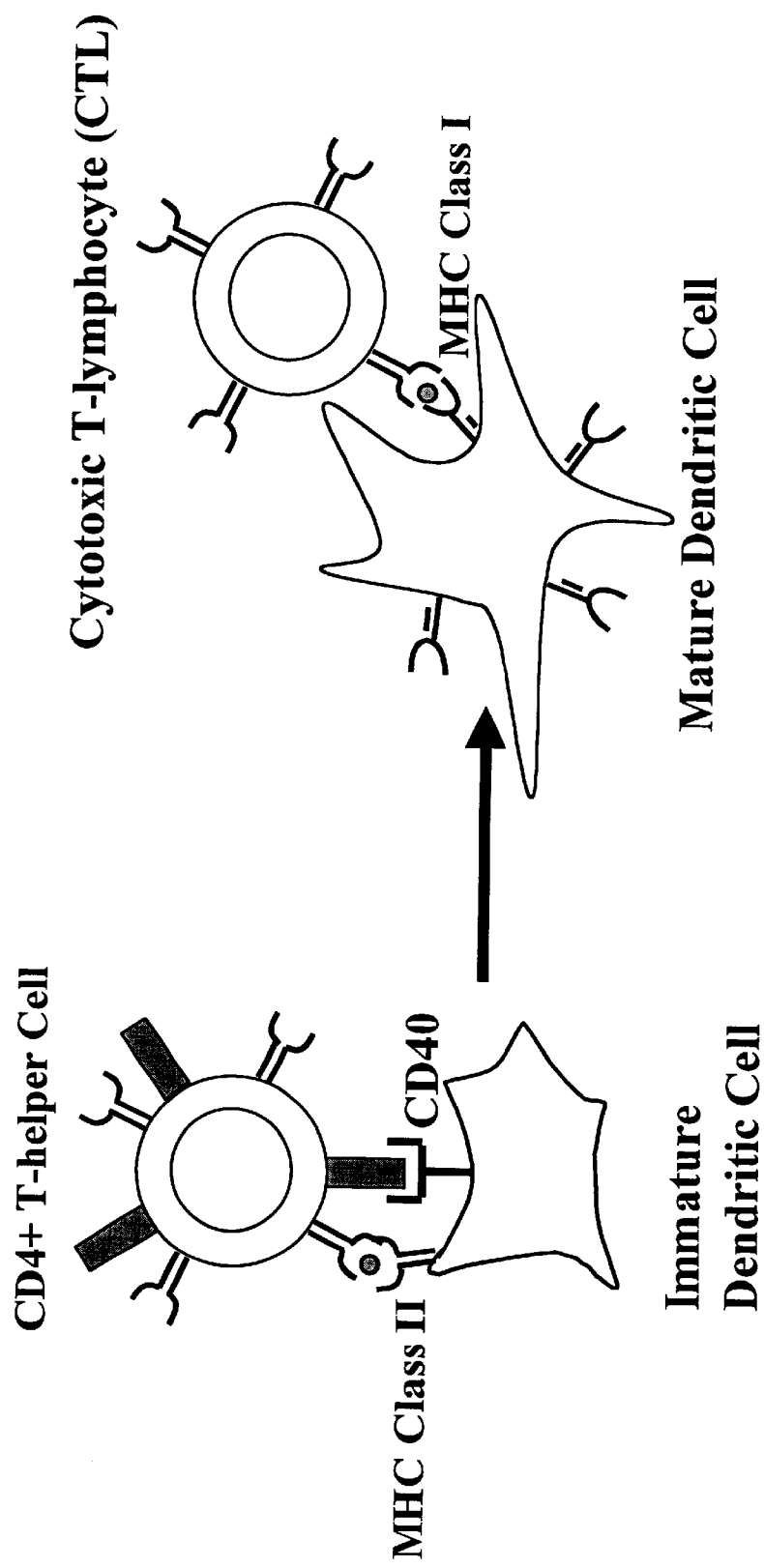
FIG. 9 shows that in nature, activation of dendritic cells is mediated by CD40-Ligand expressed on T-helper cells that enables maturation of dendritic cells such that they can properly stimulate cytotoxic T-lymphocytes (CTL's).
Figure 10:
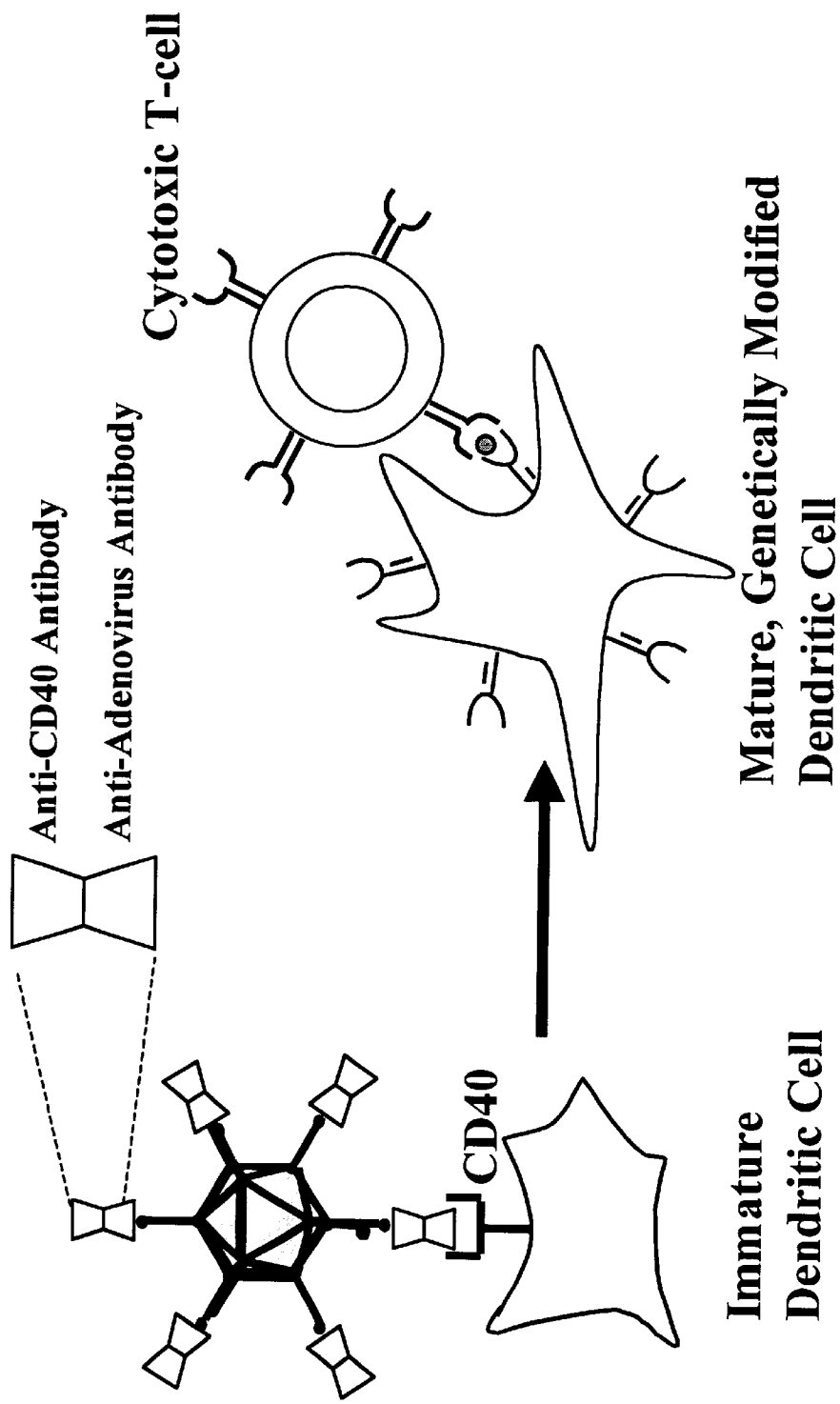
FIG. 10 shows that CD40-targeted adenovirus may substitute for CD4+ T-helper function through activation of CD40 leading to maturation of dendritic cells. For this reason, CD40-targeted adenoviral may enable stimulation of a CTL response even in the absence of functioning T-helper cells.

To overcome this deficiency, the conjugates Fab-anti-CD40 and Fab-anti β1 integrins directed against the B-cell markers CD40 and the β1 integrins, respectively, were used. Both of these conjugates were expected to reconstitute binding to replace the absence of CAR and to provide an alternative method for virion internalization into the cells. By virtue of the previously described internalizing function of these receptors, these conjugates were also anticipated to reconstitute the internalizing function of the av integrins. By use of either of these retargeting strategies, gene transfer to primary B-cells has been enhanced by a least 10-fold over untargeted adenoviral (FIG. 8). These results are particularly interesting because targeting of adenoviral to CD40 or the β1 integrins seems to have simultaneously overcome deficiency of both the primary binding receptor as well as the secondary, internalizing receptor.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A composition for delivery of a gene of interest to antigen presenting cells comprising:
   (a) an adenovirus encoding a gene of interest
   (b) a first antibody which specifically binds a fiber-knob protein on said adenovirus; and
   (c) a second antibody which specifically binds the CD40 antigen on the surface of said antigen presenting cells, wherein said first antibody and said second antibody are genetically fused to form a bispecific antibody.

2. The composition of claim 1, wherein said antibody directed to CD40 antigen is G28.5.

3. The composition of claim 1, wherein said gene delivery system can be used to transduce and immunomodulate immune system cells.

4. The composition of claim 1, wherein said gene of interest is selected from the group consisting of a gene encoding a tumor antigen, a gene encoding an antigen for an infectious agent, a gene encoding an autoimmune antigen, an immunomodulatory gene and a gene encoding a cytotoxic agent.

5. The composition of claim 1, wherein said antigen presenting cells are selected from the group consisting of dendritic cells and B-cells.

6. The composition of claim 5, wherein said B-cells are matured following contact with said composition.

* * * * *